US006649379B1

(12) United States Patent
Archer et al.

(10) Patent No.: US 6,649,379 B1
(45) Date of Patent: Nov. 18, 2003

(54) METHOD AND DEREGULATED ENZYME FOR THREONINE PRODUCTION

(75) Inventors: John A. C. Archer, Wilmington (GB); Maximillian T. Follettie, Medford, MA (US); Anthony J. Sinskey, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 07/788,114

(22) Filed: Nov. 1, 1991

Related U.S. Application Data

(63) Continuation-in-part of application No. 07/503,325, filed on Apr. 2, 1990, now Pat. No. 5,641,660, which is a continuation of application No. 07/062,552, filed on Jun. 12, 1987, now abandoned.

(51) Int. Cl.[7] .......................... C12P 13/08; C12N 15/63; C07K 14/245; C07K 14/32
(52) U.S. Cl. ................... 435/106; 435/69.1; 435/320.1; 435/115; 435/190; 435/252.3; 435/252.33; 435/243; 530/350; 530/324; 530/326; 536/23.1; 536/23.7
(58) Field of Search .............................. 435/172.3, 69.1, 435/115, 190, 320.1, 106, 252.3, 252.31, 252.33, 243; 530/350, 324, 326; 536/23.1, 23.7

(56) References Cited

U.S. PATENT DOCUMENTS

| 4,278,765 A | 7/1981 | Debabov et al. |
| 4,894,331 A | 1/1990 | Ratzkin et al. |

FOREIGN PATENT DOCUMENTS

| EP | 82104088.8 | 12/1982 |
| EP | 82112072.2 | 9/1983 |
| EP | 85112621.9 | 4/1986 |
| EP | 86300748.0 | 8/1986 |
| EP | 86107595.0 | 12/1986 |
| EP | 86112251.3 | 3/1987 |
| EP | 87101857.8 | 8/1987 |
| JP | 62-232392 | 10/1987 |
| WO | WO 87/02984 | 5/1987 |

OTHER PUBLICATIONS

Reincheid et al. (May 1991) J. Bacteriology vol. 173(10) pp. 3228–3230.*
Peoples et al. (1988) Mol. Microbiol 2(1) pp 63–72 (Abstr. only).*
Beskrovnaya et al. (1990) Grenetika 26, pp 412–417 (Abstr. only).*
Winnacker (1987) From Genes to Clones: Introduction to Gene Technology Ed. M. Weiler; Weinheim; New York; VCH, 1987.*
Sinskey et al. (1990) Metabolic Engineering of Corynebacteria, pp 315–325 In H. Heclot, J. Davies, J. Florent, L. Bobichem, G. Durond, and Penasse (Ed.), Proceedings of the Sixth International Symposium on Genetics of Industrial Microorganisms, Strasburg 1990, Societé Francaise de Microbiologie, Paris.*
Katsumata, et al., "Protoplast Transformation of Glutamate–Producing Bacteria with Plasmid DNA", *J. Bacteriol.* 159(1):306–311 (1984).
Yoshihama, et al., "Cloning Vector System for *Corynebacterium glutamicum*", J. Bacteriol. 162(2):591–597 (1985).
Morinaga, et al., "Expression of *Escherichia coli* promoters in *Brevibacterium lactotermentum* using the shuttle vector pEB003", *J. Biotechnol.* 5:305–312 (1987a).
Yoshimura, et al. "Construction of Promoter–Probe Vector for a Bacillus subtilis Host by Using the trpD+ Gene of Bacillus amyoliquefaciens", *J. of Bacteriol.* 159(3):905–912 (1984).
Follettie, et al., "Development of Recombinant DNA Technology for Corynebacterium glutamicum: Isolation and Characterization of Amino Acid Biosynthetic Genes", Presented Sep. 1986 at GIM86, Fifth International Symposium, Split, Yugoslavia.
Follettie and Sinskey, "Recombinant DNA Technology for Corynebacterium Glutamicum", Food Technol., (40)10:88–94 (Oct. 1986).
Sano et al., "L–Amino Acids" *Chem. Abstracts* 105:77571f (1986).
Nakamori et al., "Coryneform bacteria carrying recombinant plasmids and their use in the fermentative production of L–threonine and L–isoleucine" *Chem. Abstracts* 102:130461m (1985a).
Nakamori et al., "Recombinant DNA, bacteria carrying said recombinant DNA and a process for producing L–threonine on L–isoleucine using said bacteria" *Chem. Abstracts* 102:216318g (1985b).
Parsot et al., "Nucleotide sequence of thrC and of the transcription termination region of the threonie operon in Escherichia coli K12" *Nucl. Acids Res.* 11:7331–7345 (1983).
Cossart et al., "Nucleotide sequence of the thrB gene of E. coli, and it two adjacent regions; the thrAB and thrBC junctions" *Nucl. Acids Res.* 9:339–347 (1981).
Warburton et al., "Increased expression of a cloned gene by local mutagenesis of its promoter and ribosome binding site" *Nucl. Acids Res.* 11:5837–5854 (1983).

(List continued on next page.)

*Primary Examiner*—David Guzo
(74) *Attorney, Agent, or Firm*—Holland & Knight LLP (57) ABSTRACT

Mutagenesis of the gene encoding homoserine dehydrogenase (hom) for production of the amino acid threonine is described. The mutation causes an alteration in the carboxy terminus of the enzyme that interferes with end-product inhibition by threonine. The lack of end-product inhibition causes an overproduction of threonine.

9 Claims, 5 Drawing Sheets

OTHER PUBLICATIONS

Miwa et al., "Stability of Recombinant Plasmids Carrying the Threonine Operon in Escherichia coli" *Agric. Biol. Chem.* 48:2233–2237 (1984).

Nakamori et al., "Improved L–Threonine Production by the Amplification of the Gene Encoding Homoserine Dehydrogenase in *Brevibacterium lactofermentum*" *Agric. Biol. Chem.* 51:87–91 (1987).

Morinaga et al., "Threonine Production by Co–existence of Cloned Genes Coding Homoserine Dehydrogenase and Homoserine Kinase in *Brevibacterium lactofermentum*" *Agric. Biol. Chem.* 51:93–100 (1987b).

Takagi et al., "Fermentative production of threonine or isoleucine by transformed bacteria" Chem. Abstracts 106:48643w (1987).

Mateos et al., "Nucleotide sequence of the homoserine kinase (thr B) gene of *Brevibacterium lactofermentum*" *Nucl. Acids Res.* 15:3922 (1987).

Sinskey et al., "Recombinant DNA Technology for *Corynebacterium glutamicum*" Proc. 4th European Congress on Biotechnology 3:35 (Jun. 14–19, 1987).

Eikmanns, et al., "Amplification of three threonine biosynthesis genes in *Corynebacterium glutamicum* and its influence on carbon flux in different strains", *Appl. Microbiol. Biotechnol.* 34:617–622 (1991).

* cited by examiner

```
cghomdr  400  E..ERDDDARLIVVTHS.A..LESDL.......SRTVELLKLSLLLRNSTV         438
(SEQ ID NO:4)

cghom    400  E..ERDDDARLIVVTHS.A..LESDL.......SRTVELLKAKPVVKAINSVIRLERD    445
(SEQ ID NO:2)

bshom    385  K..GHDELAEIVIVTHH.T..SEADF.......SDILQNLNDLEVVQEVKSTYRVEGN    429
(SEQ ID NO:5)

ecthra   492  K..NKHIDLRVCGVANSKA..LLTNVHGLNLENWQEELAQAKEPFN.LGRLIRLVKE     543
(SEQ ID NO:6)

ecmetl   667  DLSGKDVSRKLVILAREAGYNIEPDQ.......VRVESLVPAHCEGGSIDHFFENGDE    717
(SEQ ID NO:7)
```

FIGURE 5

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 2340 base pairs
      (B) TYPE: nucleic acid
      (C) STRANDEDNESS: double
      (D) TOPOLOGY: linear    (ii) MOLECULE TYPE: DNA (genomic)

(iii) HYPOTHETICAL: NO

(iv) ANTI-SENSE: NO

(v) FRAGMENT TYPE: internal

(vi) ORIGINAL SOURCE:
      (A) ORGANISM: Corynebacterium glutamicum    (ix) FEATURE:
      (A) NAME/KEY: misc_feature
      (B) LOCATION: 2278..2279
      (D) OTHER INFORMATION: /note= "Guanine residue at position
         2278 is site of deletion in mutant."

(xi) SEQUENCE DESCRIPTION: SEQ ID NO: 1:

```
GTCGACCGCG TGAAGTCGCC CTTTAGGAGA ATTCTGACTA ACTGGAGCCA AAACTTGATC      60

CACTCGAGAG CTGTGCAGTC TCTTTTTCCT TCAATTCTGC CTGCTCGAGC TCGTAGAAGT     120

AGAGGTCTAC TTCAGTTGGT TCACCTTGCA CACAAGCATG AAGTAGTGGG TAGGTCGAGT     180

TGTTAAATGC GGTGTAGAAG GGGAGTAGTT CGCTAGCAAA GGTTAATTTG GAGTCGCTGT     240

ACTGCGGGTT CTCGGGTGGA GTATTCCCGG AGGATTCAAG AAATCTTGAC GCATCTTTGA     300

TGAGGTATGT TTGGAATTCG TCGGCACCTT CCTCGCCGGA GAGGTAGTAG GAGTTCTCGT     360

AATTTGGAAC CCAGATGGCA AATCGTGCGT TTTCGATTGC GTCCAGGACT TCCTCTACGT     420

TGTATCTCGC ACTTGTTGCA GCGGAAGCGA CTCGGTTGCC GATGTCTCCG TATGCAGTGA     480

GCGTGGCGTT TCCGAGGGGA ACTTGATCAG AGGAATACAC CATGGAGCCG ATGTCAGAGG     540

CGACTGCGGG CAGATCCTTT TGAAGCTGTT TCACAATTTC TTTGCCCAGT TCGCGGCGGA     600

TCTGGAACCA CTTTTGCATG CGATCGTCGT CAGAGTGGTT CATGTGAAAA ATACACTCAC     660

CATCTCAATG GTCATGGTGA AGGCCTGTAC TGGCTGCGAC AGCATGGAAC TCAGTGCAAT     720

GGCTGTAAGG CCTGCACCAA CAATGATTGA GCGAAGCTCC AAAATGTCCT CCCCGGGTTG     780

ATATTAGATT TCATAAATAT ACTAAAAATC TTGAGAGTTT TTCCGTTGAA AACTAAAAAG     840

CTGGGAAGGT GAATCGAATT TCGGGGCTTT AAAGCAAAAA TGAACAGCTT GGTCTATAGT     900

GGCTAGGTAC CCTTTTTGTT TTGCACACAT GTAGGGTGGC CGAAACAAAG TAATAGGACA     960

ACAACGCTCG ACCGCGATTA TTTTTGGAGA ATCATGACCT CAGCATCTGC CCCAAGCTTT    1020

AACCCCGGCA AGGGTCCCGG CTCAGCAGTC GGAATTGCCC TTTTAGGATT CGGAACAGTC    1080

GGCACTGAGG TGATGCGTCT GATGACCGAG TACGGTGATG AACTTGCGCA CCGCATTGGT    1140

GGCCCACTGG AGGTTCGTGG CATTGCTGTT TCTGATATCT CAAAGCCACG TGAAGGCGTT    1200

GCACCTGAGC TGCTCACTGA GGACGCTTTT GCACTCATCG AGCGCGAGGA TGTTGACATC    1260

GTCGTTGAGG TTATCGGCGG CATTGAGTAC CCACGTGAGG TAGTTCTCGC AGCTCTGAAG    1320
```

-continued

```
GCCGGCAAGT CTGTTGTTAC CGCCAATAAG GCTCTTGTTG CAGCTCACTC TGCTGAGCTT    1380

GCTGATGCAG CGGAAGCCGC AAACGTTGAC CTGTACTTCG AGGCTGCTGT TGCAGGCGCA    1440

ATTCCAGTGG TTGGCCCACT GCGTCGCTCC CTGGCTGGCG ATCAGATCCA GTCTGTGATG    1500

GGCATCGTTA ACGGCACCAC CAACTTCATC TTGGACGCCA TGGATTCCAC CGGCGCTGAC    1560

TATGCAGATT CTTTGGCTGA GGCAACTCGT TTGGGTTACG CCGAAGCTGA TCCAACTGCA    1620

GACGTCGAAG GCCATGACGC CGCATCCAAG GCTGCAATTT TGGCATCCAT CGCTTTCCAC    1680

ACCCGTGTTA CCGCGGATGA TGTGTACTGC GAAGGTATCA GCAACATCAG CGCTGCCGAC    1740

ATTGAGGCAG CACAGCAGGC AGGCCACACC ATCAAGTTGT TGGCCATCTG TGAGAACTTC    1800

ACCAACAAGG AAGGAAAGTC GGCTATTTCT GCTCGCGTGC ACCCGACTCT ATTACCTGTG    1860

TCCCACCCAC TGGCGTCGGT AAACAAGTCC TTTAATGCAA TCTTTGTTGA AGCAGAAGCA    1920

GCTGGTCGCC TGATGTTCTA CGGAAACGGT GCAGGTGGCG CGCCAACCGC GTCTGCTGTC    1980

CTTGGCGACG TCGTTGGTGC CGCACGAAAC AAGGTGCACG GTGGCCCTGC TCCAGGTGAG    2040

TCCACCTACG CTAACCTGCC GATCGCTGAT TTCGGTGAGA CCACCACTCG TTACCACCTC    2100

GACATGGATG TGGAAGATCG CGTGGGGGTT TTGGCTGAAT TGGCTAGCCT GTTCTCTGAG    2160

CAAGGAATCT CCCTGCGTAC AATCCGACAG GAAGAGCGCG ATGATGATGC ACGTCTGATC    2220

GTGGTCACCC ACTCTGCGCT GGAATCTGAT CTTTCCCGCA CCGTTGAACT GCTGAAGGCT    2280

AAGCCTGTTG TTAAGGCAAT CAACAGTGTG ATCCGCCTCG AAAGGGACTA ATTTTACTGA    2340
```

(2) INFORMATION FOR SEQ ID NO: 2:

(i) SEQUENCE CHARACTERISTICS:
        (A) LENGTH: 445 amino acids
        (B) TYPE: amino acid
        (C) STRANDEDNESS: single
        (D) TOPOLOGY: linear    (ii) MOLECULE TYPE: protein   (iii) HYPOTHETICAL: NO    (iv) ANTI-SENSE: NO     (v) FRAGMENT TYPE: internal    (vi) ORIGINAL SOURCE:
        (A) ORGANISM: Corynebacterium glutamicum    (xi) SEQUENCE DESCRIPTION: SEQ ID NO: 2:

```
Met Thr Ser Ala Ser Ala Pro Ser Phe Asn Pro Gly Lys Gly Pro Gly
1               5                  10                  15

Ser Ala Val Gly Ile Ala Leu Leu Gly Phe Gly Thr Val Gly Thr Glu
                20                  25                  30

Val Met Arg Leu Met Thr Glu Tyr Gly Asp Glu Leu Ala His Arg Ile
            35                  40                  45

Gly Gly Pro Leu Glu Val Arg Gly Ile Ala Val Ser Asp Ile Ser Lys
        50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Glu Val Ile Gly Gly
                85                  90                  95

Ile Glu Tyr Pro Arg Glu Val Val Leu Ala Ala Leu Lys Ala Gly Lys
                100                 105                 110

Ser Val Val Thr Ala Asn Lys Ala Leu Val Ala Ala His Ser Ala Glu
            115                 120                 125
```

Leu Ala Asp Ala Ala Glu Ala Ala Asn Val Asp Leu Tyr Phe Glu Ala
        130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
                180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
        210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
                260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
        290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Gly Arg Ala Pro Gly Glu Ser Thr Tyr
                340                 345                 350

Ala Asn Leu Pro Ile Ala Asp Phe Gly Glu Thr Thr Thr Arg Tyr His
        355                 360                 365

Leu Asp Met Asp Val Glu Asp Arg Val Gly Val Leu Ala Glu Leu Ala
        370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
        420                 425                 430

Val Lys Ala Ile Asn Ser Val Ile Arg Leu Glu Arg Asp
        435                 440                 445

(2) INFORMATION FOR SEQ ID NO: 3:

(i) SEQUENCE CHARACTERISTICS:
        (A) LENGTH: 2339 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:

-continued (A) ORGANISM: Corynebacterium glutamicum (xi) SEQUENCE DESCRIPTION: SEQ ID NO: 3:

```
GTCGACCGCG TGAAGTCGCC CTTTAGGAGA ATTCTGACTA ACTGGAGCCA AAACTTGATC      60
CACTCGAGAG CTGTGCAGTC TCTTTTTCCT TCAATTCTGC CTGCTCGAGC TCGTAGAAGT     120
AGAGGTCTAC TTCAGTTGGT TCACCTTGCA CACAAGCATG AAGTAGTGGG TAGGTCGAGT     180
TGTTAAATGC GGTGTAGAAG GGGAGTAGTT CGCTAGCAAA GGTTAATTTG GAGTCGCTGT     240
ACTGCGGGTT CTCGGGTGGA GTATTCCCGG AGGATTCAAG AAATCTTGAC GCATCTTTGA     300
TGAGGTATGT TTGGAATTCG TCGGCACCTT CCTCGCCGGA GAGGTAGTAG GAGTTCTCGT     360
AATTTGGAAC CCAGATGGCA AATCGTGCGT TTTCGATTGC GTCCAGGACT TCCTCTACGT     420
TGTATCTCGC ACTTGTTGCA GCGGAAGCGA CTCGGTTGCC GATGTCTCCG TATGCAGTGA     480
GCGTGGCGTT TCCGAGGGGA ACTTGATCAG AGGAATACAC CATGGAGCCG ATGTCAGAGG     540
CGACTGCGGG CAGATCCTTT TGAAGCTGTT TCACAATTTC TTTGCCCAGT TCGCGGCGGA     600
TCTGGAACCA CTTTTGCATG CGATCGTCGT CAGAGTGGTT CATGTGAAAA ATACACTCAC     660
CATCTCAATG GTCATGGTGA AGGCCTGTAC TGGCTGCGAC AGCATGGAAC TCAGTGCAAT     720
GGCTGTAAGG CCTGCACCAA CAATGATTGA GCGAAGCTCC AAAATGTCCT CCCCGGGTTG     780
ATATTAGATT TCATAAATAT ACTAAAAATC TTGAGAGTTT TTCCGTTGAA AACTAAAAAG     840
CTGGAAGGT GAATCGAATT TCGGGGCTTT AAAGCAAAAA TGAACAGCTT GGTCTATAGT      900
GGCTAGGTAC CCTTTTTGTT TTGCACACAT GTAGGGTGGC CGAAACAAAG TAATAGGACA     960
ACAACGCTCG ACCGCGATTA TTTTTGGAGA ATCATGACCT CAGCATCTGC CCAAGCTTT     1020
AACCCCGGCA AGGGTCCCGG CTCAGCAGTC GGAATTGCCC TTTTAGGATT CGGAACAGTC    1080
GGCACTGAGG TGATGCGTCT GATGACCGAG TACGGTGATG AACTTGCGCA CCGCATTGGT    1140
GGCCCACTGG AGGTTCGTGG CATTGCTGTT TCTGATATCT CAAAGCCACG TGAAGGCGTT    1200
GCACCTGAGC TGCTCACTGA GGACGCTTTT GCACTCATCG AGCGCGAGGA TGTTGACATC    1260
GTCGTTGAGG TTATCGGCGG CATTGAGTAC CCACGTGAGG TAGTTCTCGC AGCTCTGAAG    1320
GCCGGCAAGT CTGTTGTTAC CGCCAATAAG GCTCTTGTTG CAGCTCACTC TGCTGAGCTT    1380
GCTGATGCAG CGGAAGCCGC AAACGTTGAC CTGTACTTCG AGGCTGCTGT TGCAGGCGCA    1440
ATTCCAGTGG TTGGCCCACT GCGTCGCTCC CTGGCTGGCG ATCAGATCCA GTCTGTGATG    1500
GGCATCGTTA ACGGCACCAC CAACTTCATC TTGGACGCCA TGGATTCCAC CGGCGCTGAC    1560
TATGCAGATT CTTTGGCTGA GGCAACTCGT TTGGGTTACG CCGAAGCTGA TCCAACTGCA    1620
GACGTCGAAG GCCATGACGC CGCATCCAAG GCTGCAATTT TGGCATCCAT CGCTTTCCAC    1680
ACCCGTGTTA CCGCGGATGA TGTGTACTGC GAAGGTATCA GCAACATCAG CGCTGCCGAC    1740
ATTGAGGCAG CACAGCAGGC AGGCCACACC ATCAAGTTGT TGGCCATCTG TGAGAACTTC    1800
ACCAACAAGG AAGGAAAGTC GGCTATTTCT GCTCGCGTGC ACCCGACTCT ATTACCTGTG    1860
TCCCACCCAC TGGCGTCGGT AAACAAGTCC TTTAATGCAA TCTTTGTTGA AGCAGAAGCA    1920
GCTGGTCGCC TGATGTTCTA CGGAAACGGT GCAGGTGGCG CGCCAACCGC GTCTGCTGTC    1980
CTTGGCGACG TCGTTGGTGC CGCACGAAAC AAGGTGCACG GTGGCCCTGC TCCAGGTGAG    2040
TCCACCTACG CTAACCTGCC GATCGCTGAT TTCGGTGAGA CCACCACTCG TTACCACCTC    2100
GACATGGATG TGGAAGATCG CGTGGGGGTT TTGGCTGAAT TGGCTAGCCT GTTCTCTGAG    2160
CAAGGAATCT CCCTGCGTAC AATCCGACAG GAAGAGCGCG ATGATGATGC ACGTCTGATC    2220
GTGGTCACCC ACTCTGCGCT GGAATCTGAT CTTTCCCGCA CCGTTGAACT GCTGAAGCTA    2280
```

AGCCTGTTGT TAAGGCAATC AACAGTGTGA TCCGCCTCGA AAGGGACTAA TTTTACTGGA    2339

(2) INFORMATION FOR SEQ ID NO: 4:

(i) SEQUENCE CHARACTERISTICS:
        (A) LENGTH: 438 amino acids
        (B) TYPE: amino acid
        (C) STRANDEDNESS: single
        (D) TOPOLOGY: linear     (ii) MOLECULE TYPE: protein    (iii) HYPOTHETICAL: NO     (iv) ANTI-SENSE: NO      (v) FRAGMENT TYPE: internal     (vi) ORIGINAL SOURCE:
        (A) ORGANISM: Corynebacterium glutamicum     (xi) SEQUENCE DESCRIPTION: SEQ ID NO: 4:

```
Met Thr Ser Ala Ser Ala Pro Ser Phe Asn Pro Gly Lys Gly Pro Gly
  1               5                  10                  15

Ser Ala Val Gly Ile Ala Leu Leu Gly Phe Gly Thr Val Gly Thr Glu
             20                  25                  30

Val Met Arg Leu Met Thr Glu Tyr Gly Asp Glu Leu Ala His Arg Ile
         35                  40                  45

Gly Gly Pro Leu Glu Val Arg Gly Ile Ala Val Ser Asp Ile Ser Lys
 50                  55                  60

Pro Arg Glu Gly Val Ala Pro Glu Leu Leu Thr Glu Asp Ala Phe Ala
 65                  70                  75                  80

Leu Ile Glu Arg Glu Asp Val Asp Ile Val Glu Val Ile Gly Gly
                 85                  90                  95

Ile Glu Tyr Pro Arg Glu Val Val Leu Ala Ala Leu Lys Ala Gly Lys
                100                 105                 110

Ser Val Val Thr Ala Asn Lys Ala Leu Val Ala Ala His Ser Ala Glu
            115                 120                 125

Leu Ala Asp Ala Ala Glu Ala Ala Asn Val Asp Leu Tyr Phe Glu Ala
130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
                180                 185                 190

Ser Leu Ala Glu Ala Thr Arg Leu Gly Tyr Ala Glu Ala Asp Pro Thr
            195                 200                 205

Ala Asp Val Glu Gly His Asp Ala Ala Ser Lys Ala Ala Ile Leu Ala
210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
            275                 280                 285
```

```
Val Ser His Pro Leu Ala Ser Val Asn Lys Ser Phe Asn Ala Ile Phe
    290                 295                 300
Val Glu Ala Glu Ala Ala Gly Arg Leu Met Phe Tyr Gly Asn Gly Ala
305                 310                 315                 320
Gly Gly Ala Pro Thr Ala Ser Ala Val Leu Gly Asp Val Val Gly Ala
                325                 330                 335
Ala Arg Asn Lys Val His Gly Gly Arg Ala Pro Gly Glu Ser Thr Tyr
            340                 345                 350
Ala Asn Leu Pro Ile Ala Asp Phe Gly Glu Thr Thr Thr Arg Tyr His
            355                 360                 365
Leu Asp Met Asp Val Glu Asp Arg Val Gly Val Leu Ala Glu Leu Ala
    370                 375                 380
Ser Leu Phe Ser Glu Gln Gly Ile Ser Leu Arg Thr Ile Arg Gln Glu
385                 390                 395                 400
Glu Arg Asp Asp Asp Ala Arg Leu Ile Val Val Thr His Ser Ala Leu
                405                 410                 415
Glu Ser Asp Leu Ser Arg Thr Val Glu Leu Leu Lys Leu Ser Leu Leu
            420                 425                 430
Leu Arg Gln Ser Thr Val
        435
```

(2) INFORMATION FOR SEQ ID NO: 5:

(i) SEQUENCE CHARACTERISTICS:
        (A) LENGTH: 46 amino acids
        (B) TYPE: amino acid
        (C) STRANDEDNESS: single
        (D) TOPOLOGY: linear     (ii) MOLECULE TYPE: protein     (iii) HYPOTHETICAL: NO     (iv) ANTI-SENSE: NO     (v) FRAGMENT TYPE: internal     (vi) ORIGINAL SOURCE:
        (A) ORGANISM: Bacillus subtilis     (xi) SEQUENCE DESCRIPTION: SEQ ID NO: 5:

```
Lys Gly His Asp Glu Leu Ala Glu Ile Val Ile Val Thr His His Thr
1               5                   10                  15
Ser Glu Ala Asp Phe Ser Asp Ile Leu Gln Asn Leu Asn Asp Leu Glu
            20                  25                  30
Val Val Gln Glu Val Lys Ser Thr Tyr Arg Val Glu Gly Asn
        35                  40                  45
```

(2) INFORMATION FOR SEQ ID NO: 6:

(i) SEQUENCE CHARACTERISTICS:
        (A) LENGTH: 52 amino acids
        (B) TYPE: amino acid
        (C) STRANDEDNESS: single
        (D) TOPOLOGY: linear     (ii) MOLECULE TYPE: protein     (iii) HYPOTHETICAL: NO     (iv) ANTI-SENSE: NO     (v) FRAGMENT TYPE: internal     (vi) ORIGINAL SOURCE:

(A) ORGANISM: Escherichia coli (xi) SEQUENCE DESCRIPTION: SEQ ID NO: 6:

```
Lys Asn Lys His Ile Asp Leu Arg Val Cys Gly Val Ala Asn Ser Lys
1               5                   10                  15

Ala Leu Leu Thr Asn Val His Gly Leu Asn Leu Glu Asn Trp Gln Glu
                20                  25                  30

Glu Leu Ala Gln Ala Lys Glu Pro Phe Asn Leu Gly Arg Leu Ile Arg
            35                  40                  45

Leu Val Lys Glu
        50
```

(2) INFORMATION FOR SEQ ID NO: 7:

(i) SEQUENCE CHARACTERISTICS:
        (A) LENGTH: 51 amino acids
        (B) TYPE: amino acid
        (C) STRANDEDNESS: single
        (D) TOPOLOGY: linear    (ii) MOLECULE TYPE: protein   (iii) HYPOTHETICAL: NO    (iv) ANTI-SENSE: NO     (v) FRAGMENT TYPE: internal    (vi) ORIGINAL SOURCE:
        (A) ORGANISM: Escherichia coli    (xi) SEQUENCE DESCRIPTION: SEQ ID NO: 7:

```
Asp Leu Ser Gly Lys Asp Val Ser Arg Lys Leu Val Ile Leu Ala Arg
1               5                   10                  15

Glu Ala Gly Tyr Asn Ile Glu Pro Asp Gln Val Arg Val Glu Ser Leu
                20                  25                  30

Val Pro Ala His Cys Glu Gly Gly Ser Ile Asp His Phe Phe Glu Asn
            35                  40                  45

Gly Asp Glu
        50
```

METHOD AND DEREGULATED ENZYME FOR THREONINE PRODUCTION

This is a continuation-in-part application of U.S. patent application Ser. No. 07/503,325 filed Apr. 2, 1990, now U.S. Pat. No. 5,641,660, which is incorporated by reference herein, which is a continuation of U.S. Ser. No. 07/062,552 entitled "C. glutamicum Threonine Biosynthetic Pathway" filed Jun. 12, 1987, by A. J. Sinskey, M. T. Follettie, M. T. Liebl, and O. P. Peoples, now abandoned.

BACKGROUND OF THE INVENTION

This invention is generally in the area of biochemistry and is specifically directed to production of the amino acid threonine.

Amino acids are often referred to as the building blocks of proteins. Amino acids also serve as sources of nitrogen and sulfur and can be catabolized to provide energy. There are twenty common amino acids all containing at least one carbon atom covalently bonded to a carboxyl group (COOH), an amino group ($NH_3$), hydrogen (H) and a variable side chain (R).

Amino acids are necessary for the survival of all organisms. Some amino acids are synthesized by the organism while others are provided in the diet. Enzymes transform biomolecules into amino acids, degrade amino acids, and convert amino acids from one type to another. The absence or excess of an amino acid in humans can cause a clinical disorder such as Phenylketonuria, Cystinuria, Fanconi's syndrome or Hartnup disease. Treatment for these disorders currently involves dietary restrictions to reduce intake of the amino acids found in excess and supplementation of the deficient amino acids. The production of large quantities of purified amino acids is essential for scientific research involving amino acid metabolism and treatment of amino acid disorders.

Figure 1:
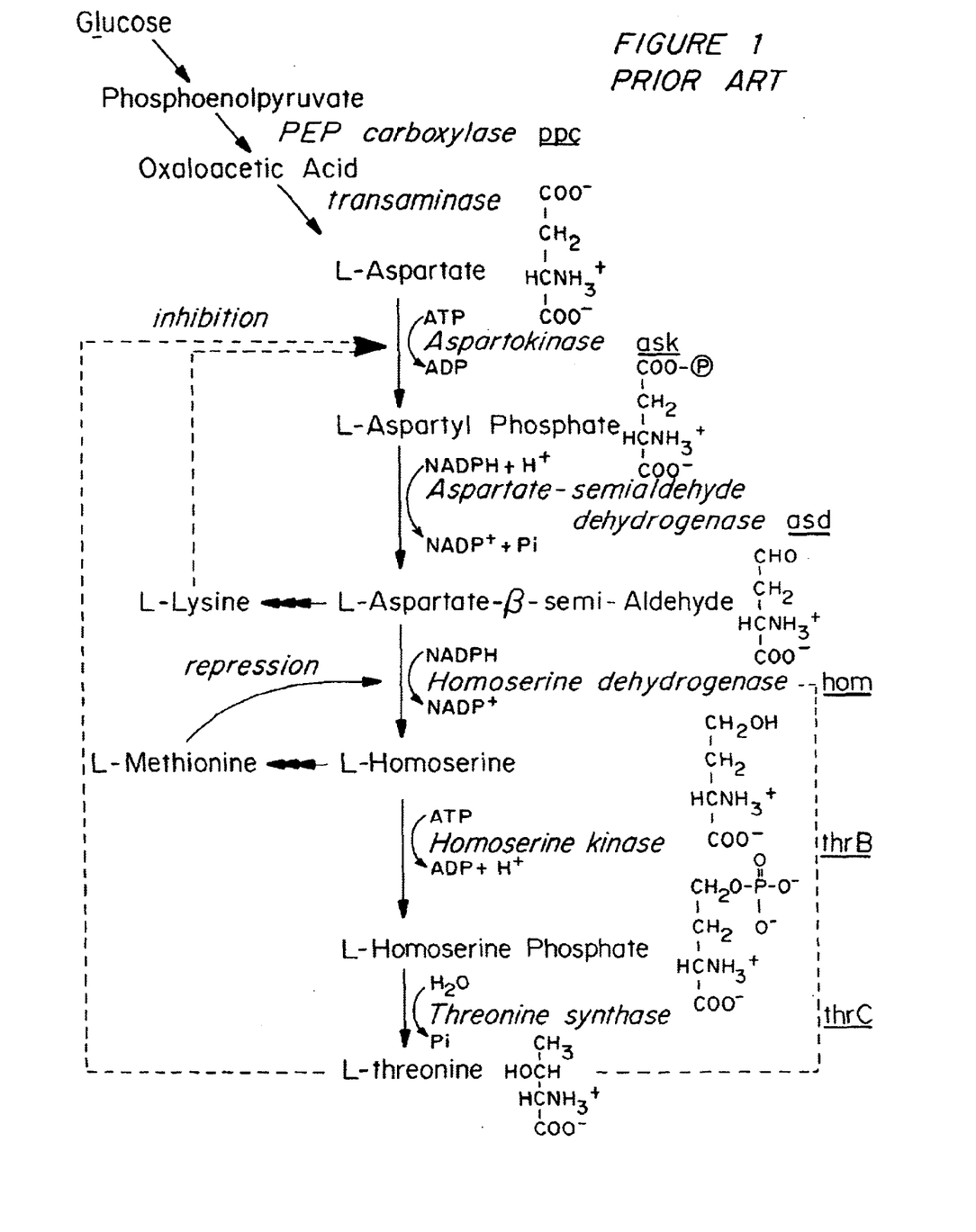
FIG. 1 (Prior Art) is a schematic diagram of the biosynthesis of threonine from aspartate showing chemical structures and end-product inhibition. Enzyme activities are shown in italic font, substrates and products are shown in Roman font. Allosteric feedback inhibition control is shown with dashed arrows.

The amino acid threonine has an uncharged polar R group containing a hydroxyl group. The synthesis of threonine proceeds from the substrate aspartate via the branched amino acid biosynthetic pathway as shown in FIG. 1. Aspartate is synthesized from oxaloacetate, a product of glucose metabolism through the tricarboxylic acid cycle. Briefly, oxaloacetate is converted to L-aspartate by a transaminase. L-aspartate is converted to β-aspartylphosphate by aspartokinase which is dehydrogenated to L-aspartic-β-semialdehyde which is, in turn, dehydrogenated to L-homoserine by homoserine dehydrogenase encoded by the gene hom. Homoserine kinase encoded by the gene thrB converts L-homoserine to O-phospho-L-homoserine. Threonine synthase encoded by the gene thrC converts O-phospho-L-homoserine to the amino acid L-threonine.

Attempts have been made to produce threonine from bacteria. European Patent Application No. 82104088.8 entitled "Method for Producing L-Threonine by Fermentation" describes high yield producing strains of Corynebacterium produced by recombinant techniques. The antimetabolite α-amino-β-hydroxy-valeric acid is used to screen strains for threonine over-production. Cells resistant to α-amino-β-hydroxy-valeric acid toxicity are generally high producers of threonine. Genomic DNA from these resistant strains are inserted into Corynebacterium compatible plasmids and used to transform α-amino-β-hydroxy-valeric acid sensitive strains to produce resistant clones. The gene or genes controlling resistance are not identified or characterized, and threonine production is only achieved with the isolated, resistant strain disclosed. The publication of Eikmanns et al., *Appl. Microbiol. Biotechnol.*, 34:617:622 (1991) similarly describes a mutant of the hom gene designated $hom_{fbr}$, a homoserine dehydrogenase gene resistant to feedback inhibition by threonine. The $hom_{fbr}$-thrB operon of *C. glutamicum* is expressed in corynebacterial strains for the production of threonine. However, neither the site nor the region of the mutation causing resistance to feedback inhibition is identified or characterized.

The threonine biosynthetic pathway has been studied extensively in bacteria such as the Gram-positive bacterium *Corynebacterium glutamicum* (*C. glutamicum*), *Escherichia coli* (*E. coli*) and *Bacillus subtilis* (*B. subtilis*). Although threonine is synthesized via the same reaction path shown in FIG. 1 in all three bacteria, the genetic and biochemical organization responsible for the enzymes homoserine dehydrogenase, homoserine kinase, and threonine synthase differ in each organism.

In Corynebacterium such as *C. glutamicum*, and *C. flavum*, the homoserine dehydrogenase and homoserine kinase enzymes are encoded by a two-gene operon hom-thrB, as described by the publications of Follettie et al., Organization and regulation of the *Corynebacterium glutamicum* hom-thrB and thrC loci, *Mol. Microbiol.* 2:53–62 (1988) and Peoples et al., Nucleotide sequence and fine structural analysis of the *Corynebacterium glutamicum* hom-thrB operon, *Mol. Microbiol.* 2:63–72 (1988), and U.S. Ser. No. 07/062,552 filed Jun. 12, 1987. Transcription of the hom-thrB operon is repressed. by the amino acid methionine while the activity of homoserine dehydrogenase is allosterically inhibited by the amino acid end product threonine.

The *E. coli* threonine operon (thrABC) encodes four enzyme activities, namely a bi-functional polypeptide, aspartokinase-I-homoserine dehydrogenase-I, a monofunctional homoserine kinase and a threonine synthase. A second bi-functional protein, aspartokinase-II-homoserine dehydrogenase-II, is encoded by the metL gene. Expression of the thrABC operon is controlled by threonine-isoleucine mediated attenuation. Both of the activities encoded by the thrA gene, aspartokinase-I-homoserine dehydrogenase-I, are allosterically inhibited by the amino acid threonine.

The *B. subtilis* homoserine dehydrogenase, threonine synthase and homoserine kinase genes are closely linked in the order hom-thrC-thrB and most likely form an operon. The homoserine dehydrogenase enzyme is repressed by the amino acids threonine and methionine.

In all three bacteria, regulation of threonine synthesis is accomplished by end-product inhibition of the first enzyme in the threonine pathway, the enzyme homoserine dehydrogenase, encoded by the gene hom or thrA. The phenomenon of allosteric inhibition of the monofunctional homoserine dehydrogenase enzyme of *C. glutamicum* is characterized in the publication of Follettie et al., *Mol. Microbiol.* 2:53–62 (1988). Threonine inhibits the enzyme with an inhibition rate constant (Ki) of 0.16 mM. Most likely, threonine inhibits the enzymatic activity of homoserine dehydrogenase by binding to a binding site on the enzyme.

Peoples et al., *Mol. Microbiol.* 2:63–72 (1988), have sequenced the hom gene of *C. glutamicum* which encodes homoserine dehydrogenase and from this sequence have determined an amino acid sequence encoding a 43,000 dalton polypeptide. The *C. glutamicum* homoserine dehydrogenase exhibits 27% and 31% homology with the *E. coli* and *B. subtilis* homoserine dehydrogenase amino acid sequences respectively.

Attempts have been made to utilize the genes encoding the enzymes involved in threonine biosynthesis to achieve threonine over-production. Morinaga et al., *Agric. Biol. Chem.* 51:93–100 (1987) describe transformation of bacterial cells with a plasmid containing both the gene for homoserine kinase from a threonine-producing mutant bacterial strain and the gene for homoserine dehydrogenase. Miwa et al. *Agric. Biol. Chem.* 48:2233–2237 (1984) describe a recombinant *E. coli* strain transformed with a recombinant plasmid containing the threonine operon (thrA, thrB and thrC,) of *E. coli*. Nakamori et al., *Chem. Abstracts* 102:216318g (1985) transform *Brevibacterium lactofermentum* with a recombinant plasmid containing the gene for homoserine kinase. Nakamori et al., *Agric. Biol. Chem.* 51:87–91 (1987) transform *Brevibacterium lactofermentum* with a recombinant plasmid containing the gene for homoserine dehydrogenase from B. lactofermentum M-15, a threonine and lysine-producing mutant. Takagi et al., *Chem. Abstracts* 106:48643w (1987) transform coryneform bacteria with a recombinant plasmid containing homoserine kinase-encoding genes. The problems with these methods of producing threonine is that the mutations are not characterized, and the resulting plasmids are inherently unstable, resulting in transformed bacteria that are genetically fragile.

What is needed is a method of producing threonine that involves a characterized structural mutation. A mutation of the homoserine dehydrogenase gene that prevents end-product inhibition by threonine should result in deregulated threonine biosynthesis.

It is therefore an object of the present invention to provide a method for the over-production of threonine.

It is a further object of the present invention to provide a method for the production of threonine utilizing a structural mutant.

It is a further object of the present invention to provide a mutation in the homoserine dehydrogenase gene that renders the enzyme insensitive to end-product inhibition.

It is a further object of the present invention to provide a deregulated homoserine dehydrogenase.

SUMMARY OF THE INVENTION

A method for the production of threonine and the construction, isolation and cloning of a deregulated homoserine dehydrogenase gene in bacteria is described. A mutation in the gene encoding homoserine dehydrogenase (hom) that causes an alteration in the carboxy terminus of the enzyme interferes with end-product inhibition by threonine. The lack of end-product inhibition causes an over-production of threonine.

BRIEF DESCRIPTION OF THE DRAWINGS

FIG. 2 is a schematic depiction of sub-cloning strategy and restriction maps. The plasmid pJD1 is an *E. coli* replicon pUC18 containing the 4.1 Kb EcoRI R102 genomic DNA encoding hom$^{dr}$-thrB. The plasmid pMF33 is a broad host range pSR1 replicon exhibiting kanamycin resistance. The plasmid pJD4 is a *C. glutamicum/E. coli* cloning vector pMF33 containing the 3.3 Kb SalI restriction fragment of pJD1 encoding hom$^{dr}$-thrB. The solid black bar represents pSR1 sequences; the shaded bar represents pUC18 sequences; the thin-hatched bar represents Tn903 sequences; the thick-hatched bar represents R102 sequences; and the arrow represents the direction of transcription.

DETAILED DESCRIPTION OF THE INVENTION

A method for the production of the amino acid threonine and the construction, isolation and cloning of a mutant homoserine dehydrogenase that is insensitive to threonine allosteric inhibition are described. A deregulated mutant homoserine dehydrogenase gene designated hom$^{dr}$ was isolated from the *C. glutamicum* genome and sequenced. A mutation in the carboxy terminal of the gene results in expression of a truncated homoserine dehydrogenase protein that escapes end-product regulation by threonine, resulting in threonine over-production.

Methods used in the production and isolation of this mutant can also be used in the production and isolation of other mutants, as described below.

Sequence 1 is the nucleotide sequence of horn (SEQ ID NO:1). Sequence 2 is the predicted amino acid sequence of horn (SEQ ID NO:2). Sequence 3 is the nucleotide sequence of the hom mutant hom$^{dr}$ (SEQ ID NO:3). Sequence 4 is the predicted amino acid sequence of the horn mutant hom$^{dr}$ (SEQ ID NO:4).

Isolation of Homoserine Dehydrogenase Mutant Strains

Cells, preferably the cells of bacteria such as *C. glutamicum, E. Coli* and *B. subtilis*, are mutated with a mutagen such as ultraviolet radiation. Most preferably the cells are *C. glutamicum* AS019 cells, a rifampicin resistant prototroph of *C. glutamicum* on deposit with the American Type Culture Collection (ATCC) under ATCC Accession Number 13059. Ultraviolet mutagenesis is preferred over other chemical mutagenic agents because it tends to produce small deletions in the target DNA. Irradiation is preferably performed such that approximately 50% of the irradiated cells are killed.

Mutants producing elevated levels of threonine are screened, preferably by growing the cells on a selective medium such as Minimal Medium *C. glutamicum* (MMCG) plates supplemented with α-hydroxy-valerate, an antimetabolite of threonine. MMCG is a defined medium well known to those skilled in the art and described in the publication of von der Osten et al. *Biotechnol. Letts.* 11:11–16 (1989). Only cells producing an excess of threonine will survive on a medium supplemented with α-hydroxy-valerate. UV mutagenesis and screening for growth on ever higher levels of α-hydroxy-valerate is continued as necessary.

To enrich for mutations within-the threonine pathway, a bioassay is preferably used. An increase in the. level of threonine production, a consequence of deregulation of homoserine dehydrogenase, can be approximated by the level of cross-feeding the threonine auxotroph indicator strain AS155. The AS155 indicator strain is described in the publication of Follettie et al., *Mol. Microbiol.* 2:53–62 (1988). Homoserine dehydrogenase activity and sensitivity to L-threonine of isolates that promote growth of the indicator strain after approximately 24 hours is preferably assessed by enzyme assay of crude cell extracts.

A deregulated mutant that is insensitive to threonine, but maintains normal ability to convert-L-aspartic-β-semialdehyde to homoserine, was isolated from *C. glutamicum* AS019, and designated R102. This mutant is tolerant to at least 20 mg/ml α-hydroxy-valerate. It encodes a homoserine dehydrogenase activity which is insensitive to threonine, but wild type with respect to its specific activity. The deregulated homoserine dehydrogenase gene ($hom^{dr}$) was cloned from the isolated mutant as described below.

Cloning the Deregulated hom Gene

A plasmid cloning vector, the ampicillin-resistant vector pUC18, was used to clone the gene for the deregulated homoserine dehydrogenase from a restriction fragment of the mutant genome, a 4.1 Kb EcoRI restriction fragment into pUC18. The ligation reaction was used to transform *E. coli* JM83 cells to ampicillin resistance. JM83 cells have the genotype ara, D(lac-proAB), rpoD, theta80d lacZM15. Recombinant plasmids carrying the 4.1 Kb EcoRI chromosomal DNA fragment were identified by in situ hybridization with a radiolabelled restriction fragment of the wild type hom-thrB operon.

Figure 2:
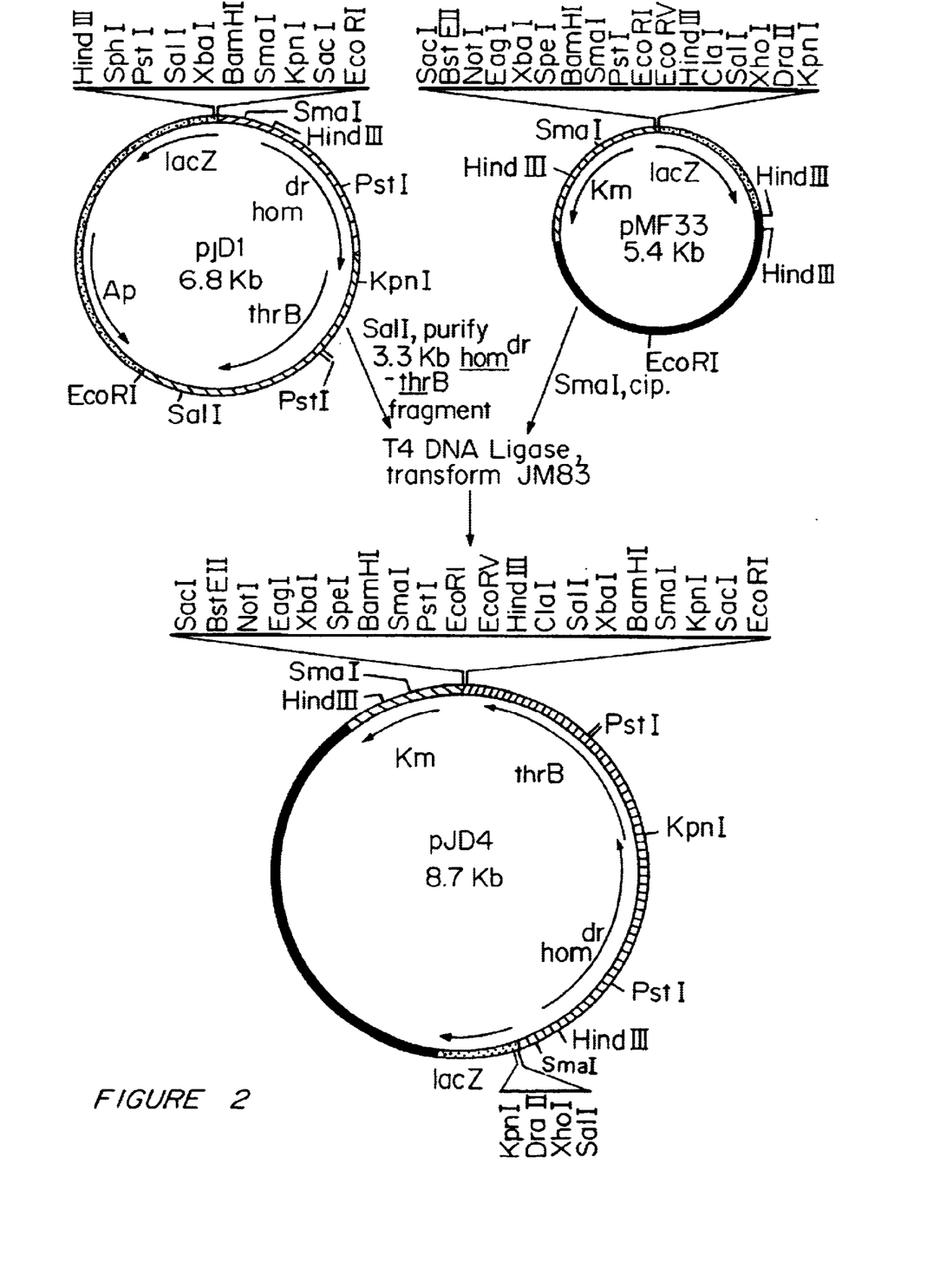

The plasmid designated pJD1 contains the positive clone. The restriction map of pJD1 is shown in FIG. 2. The plasmid pJD1 carries the $hom^{dr}$-thrB counter to the adjacent plasmid lacZ promoter. In this orientation, the expression of the $hom^{dr}$-thrB operon is controlled by its own promoter located between the SmaI and HindIII restriction sites.

Expression of $hom^{dr}$ in *C. glutamicum*

The $hom^{dr}$-thrB operon encoded on the plasmid pJD1 was subcloned into the plasmid pMF33 as shown in FIG. 2. The plasmid pMF33 is a well known, broad host range, pSR1 replicon, kanamycin resistant *C. glutamicum-E. coli* plasmid. The operon is inserted counter to the lac promoter in pMF33. This plasmid was designated pJD4 as shown in FIG. 2.

Verified pJD4/AS019EI2 transformants were selected for the presence of the plasmid by growth on kanamycin supplemented mediums. The activity of the homoserine dehydrogenase from crude cell extracts of these cultures was determined in the presence and absence of L-threonine. A host cell encoding wild type homoserine dehydrogenase would be inactivated in the presence of 10 mM L-threonine. The detection of homoserine dehydrogenase activity in the presence of 10 mM L-threonine indicated that the enzyme was deregulated. Therefore, homoserine dehydrogenase activity in the presence of L-threonine was derived from the cloned $hom^{dr}$ gene. The specific activity of the deregulated homoserine dehydrogenase is approximately the same as that reported for the *C. glutamicum* chromosomal hom gene (0.0450 μM ml$^{-1}$min$^1$) The cloned $hom^{dr}$ gene product was functional even in the presence of 120 mM L-threonine.

Sequence Analysis of hom Gene

Figure 4:
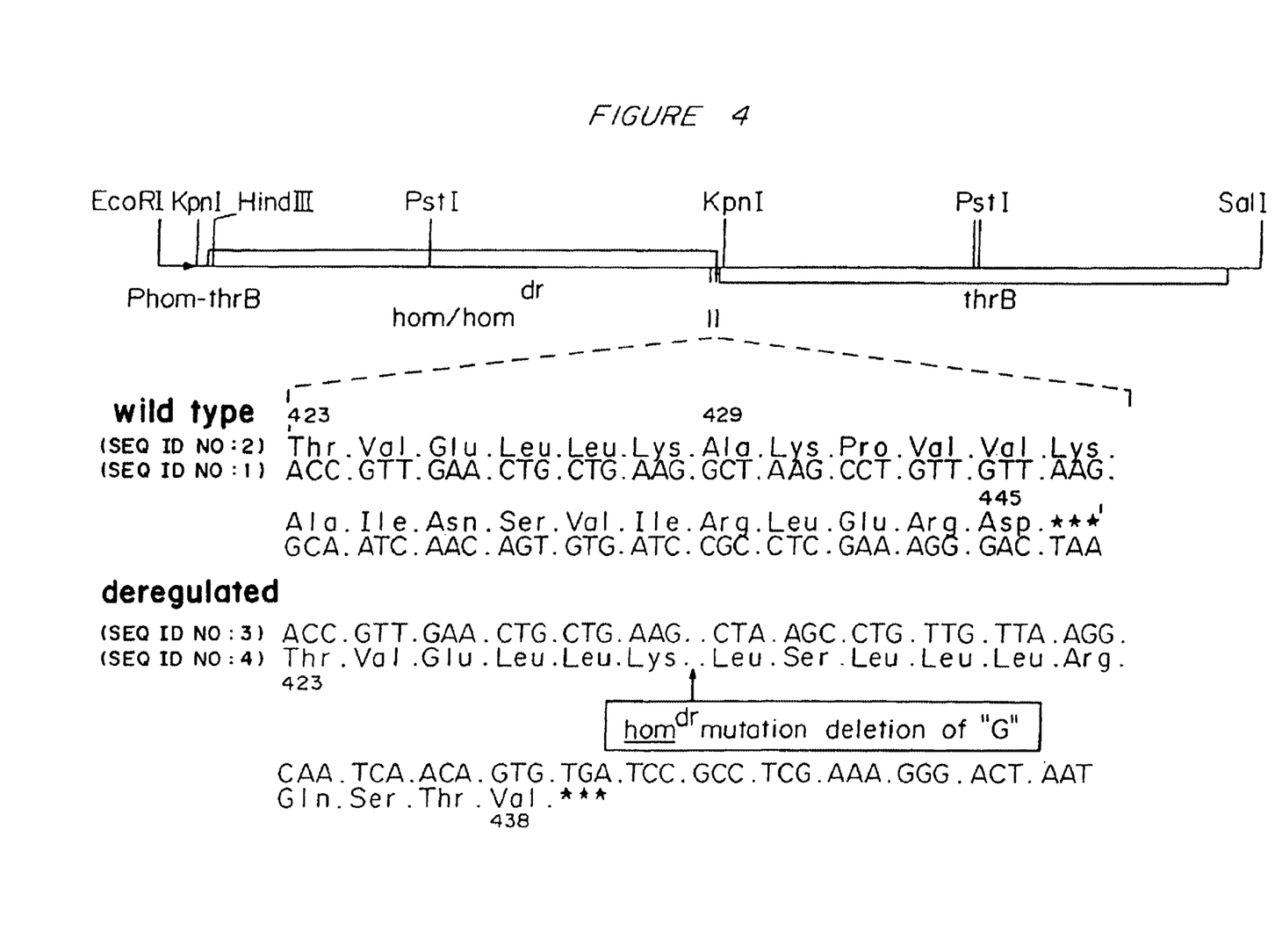
FIG. 4 is a cartoon of the R102 and AS019 homoserine dehydrogenase and homoserine kinase structural operon showing the location of the preferred single base-change associated with the hom$^{dr}$ mutation in the carboxy terminus. The predicted amino acid sequence of the deregulated enzyme is compared to the wild type enzyme amino acid sequence in the exploded view.

The complete nucleotide sequence of the $hom^{dr}$ gene (Sequence 3) and its promoter region was determined by the Sanger dideoxy method. A comparison of a preferred embodiment of the deregulated gene with the wild type revealed a single nucleotide sequence change at the carboxy terminus of the hom gene, a deletion of the guanosine (G) base at coordinate 1964 relative to the upstream EcoRI site. The sequence immediately surrounding the site of this hom mutation is shown in FIG. 4. The promoter, operator and the thrB gene are conserved. However, the single base pair deletion at 1964 bp disrupts the $hom^{dr}$ reading frame at codon 429. This frame shift mutation induces approximately ten amino acid changes and a premature termination, or truncation, i.e. deletion of approximately the last seven amino acid residues of the polypeptide.

It is believed that the single base deletion in the carboxy terminus of the $hom^{dr}$ gene radically alters the protein sequence of the carboxyl terminus of the enzyme, changing its conformation in such a way that the interaction of threonine with a binding site is prevented.

It will be understood by those skilled in the art that any mutation in the carboxy terminus of the $hom^{dr}$ gene that prevents end-product inhibition of threonine can be used in a method for the over-production of threonine as described herein.

The following non-limiting example will demonstrate isolation and characterization of a homoserine dehydrogenase mutant $hom^{dr}$ and its gene product, deregulated homoserine dehydrogenase.

EXAMPLE 1

Isolation of *C. glutamicum* Strain R102
Bacterial Strains and Plasmid Constructions The plasmid maps of the plasmids constructed in this example are shown in FIG. 2. Plasmid pMF33, which was used to express $hom^{dr}$, is a kanamycin resistant broad host range derivative of the *C. glutamicum* plasmid pSR1 that is capable of replication in both *E. coli* and *C. glutamicum* as described by Archer et al., *Biology of Corynebacterium glutamicum: A molecular approach*. in Genetics and Molecular Biology of Industrial Microorganisms. Washington, American Society for Microbiology (1989). Plasmid pJD1 is a pUC18 derivative containing the 4.1 Kb EcoRI R102 chromosomal restriction fragment encoding $hom^{dr}$-thrB. Plasmid pJD4 was constructed by ligation of the 3.3 Kb SalI restriction fragment of pJD1 carrying the $hom^{dr}$-thrB operon with its promoter into the unique SalI site of pMF33. The $hom^{dr}$-thrB operon is oriented counter to the lac promoter of pMF33 in pJD4.

Growth Media and Chemicals

*E. coli* cells were cultured in liquid medium and agar supplemented where necessary with 50 μg/ml kanamycin. *C. glutamicum* was grown in liquid broth medium and Minimal Medium, *C. glutamicum* (MMCG), a defined medium described by von der Osten et al., *Biotechnol. Letts.* 11:11–16 (1989), supplemented with 50 μg/ml kanamycin when required. The antimetabolite DL-alpha-hydroxy-valerate was prepared-by Carlos Barbas, Texas A&M University (College Station, Tex.). The substrate for homoserine dehydrogenase assays, aspartate-beta-semialdehyde, was synthesized from allylglycine according to the method of Black and Wright, *J. Biol. Chem.* 213:39–50 (1955).

Mutagenesis

Cells were pelleted from a 10 ml exponential phase ($OD_{600}$=1.0–1.2) MMCG culture of *C. glutamicum* AS019 (a rifampicin resistant prototroph of *C. glutamicum* designated ATCC accession number 13059) and washed twice in 10 ml of KCl/phosphate buffer (0.5 M KCl/0.1 M $KPO_4$, pH=7.0) in accordance with the method of Sambrok et al., Molecular Cloning: A Laboratory Manual. Cold Spring Harbor, Cold Spring Harbor Laboratory Press (1987). The cells were re-suspended in 1 ml of the same buffer and exposed to 254 nm UV irradiation at a distance of 20 cm for 15 second increments up to 90 seconds. The irradiated cells were serially diluted in phosphate buffer and plated on 10 ml Minimal Medium *C. glutamicum* (MMCG) agar supplemented with between 0.5 and 20 mg/ml alpha-hydroxy-valerate. Colonies resistant to alpha-hydroxy-valerate were picked after a 24 hour incubation at 30° C. and inoculated into 10 ml MMCG liquid for screening. Subsequent mutagenesis was performed using 60 second exposure which produce 50% killing. Mutations affecting the threonine pathway were identified by the threonine production bioassay described below.

Threonine Production Bioassay

Figure 3:
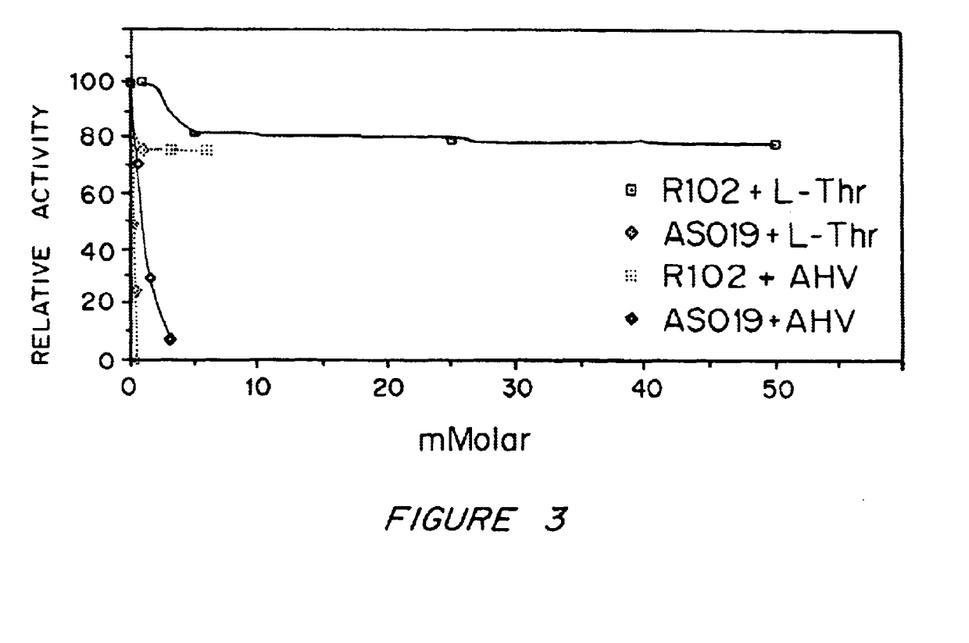
FIG. 3 is a graph of relative homoserine dehydrogenase activity measured in crude *C. glutamicum* cell extracts obtained from strains AS019 and its derivative R102 in the presence and absence of L-threonine (L-thr) and DL-α-hydroxy-valerate (AHV) in mMolar. Open square, R102+L-Thr; dark diamond, AS019+L-Thr; dark square, R102+AHV; and open diamond, AS019+AHV.

One ml of the supernatant from an overnight 10 ml MMCG culture of an alpha-hydroxy-valerate tolerant *C. glutamicum* isolate was filter sterilized and added 1:10 to a fresh 10 ml MMCG medium. This was inoculated with the test strain *C. glutamicum* AS155, a-threonine auxotroph (a hom mutant of AS019). Growth of AS155 was determined by densitometry after a 24 hour incubation at 30° C. The *C. glutamicum* AS019 mutant derivative, R102, was isolated with a tolerance to at least 20 mg/ml alpha-hydroxy-valerate. The activity of homoserine dehydrogenase in crude cell extracts of *C. glutamicum* R102 and AS019 in the presence of both threonine and alpha-hydroxy-valerate was measured. Crude cell lysates for homoserine dehydrogenase assays were prepared from 500 ml MMCG *C. glutamicum* AS019 and R102 cultures. The cells were lysed by passage through a French Pressure cell. Homoserine dehydrogenase activity was assayed by determining the initial decrease in the absorbance at 340 nm by NADPH as described by Follettie et al., *Mol. Microbiol.* 2:53–62 (1988). R102 encoded a homoserine dehydrogenase activity which was insensitive to threonine as shown in FIG. 3, but wild type with respect to its specific activity as shown in Table 1 below.

TABLE 1

Over-expression of cloned deregulated homoserine dehydrogenase in *C. glutamicum* AS019E12

| Strain/Plasmid | Specific Activity ($\mu$M NADPH $ml^{-1}min^{-1}$) | |
| --- | --- | --- |
|  | +L-threonine (10 mM) | −L-threonine |
| AS019E12/pMF33 | 0.0 | 0.045 |
| AS019E12/pJD4 | 0.507 | 0.597 |
| AS019 | 0.0 | 0.045 |
| R102 | 0.050 | 0.059 |

R102 therefore encodes a deregulated homoserine dehydrogenase enzyme that is desensitized to L-threonine and alpha-hydroxy-valerate but retains the normal catalytic functions for the protein. The deregulated homoserine dehydrogenase gene ($hom^{dr}$) was cloned from the R102 mutant as described below.

Cloning and Isolation of $hom^{dr}$ from Strain R102

The $hom^{dr}$ gene was cloned from *C. glutamicum* strain R102 and isolated in *E. coli* using the plasmid cloning vector pUC18, a pMB1 replicon, laczalpha, ampicillin resistant plasmid. The $hom^{dr}$-thrB locus of R102 was cloned as a 4.1 Kbg EcoRI restriction fragment.

Chromosomal DNA was prepared from *C. glutamicum* R102 and AS019 as follows. A 10 ml liquid broth overnight culture of *C. glutamicum* (R102 or AS019) was inoculated 1:100 into 100 ml of liquid broth and grown with shaking overnight at 30° C. The cells were washed in 20 ml 20 mM Tris-HCl pH 8.0, and re-suspended in 10 ml of the same buffer. Protoplasts were made by the stepwise addition of 10 ml 24% polyethylene glycol, 6000 Mr, 2 ml 50 mg/ml lysozyme followed by incubation at 37° C. for one hour. The protoplasted cells were harvested and re-suspended in 20 ml 100 mM Tris, 10 mM EDTA, pH 8.0, and lysed by the addition of 2 ml 10% sodium dodecyl sulphate and incubated at 55° C. until lysis was complete. The cellular debris were removed by centrifugation at 18,000×g at 4°C. The chromosomal DNA was purified from the cleared lysate by cesium chloride (CsCl) gradient ultracentrifugation.

R102 chromosomal DNA was digested to completion with EcoRI. The restriction fragments sized from 3.5 to 5.5 Kb were purified from a 0.6% preparative agarose gel. Bethesda Research Laboratories (Bethesda, Md.). These restriction fragments were ligated with pUC18 which had been linearized and dephosphorylated at the polylinker EcoRI site. The ligation reaction was used to transform *E. coli* JM83 cells to ampicillin resistance. JM83 cells have the genotype ara, delta(lac-proAB), rpoD, theta80d,lacZM15.

Restriction endonucleases and T4 DNA ligase were supplied with the appropriate buffers by Bethesda Research Laboratories (Bethesda, Md.). Chromosomal restriction digests of R102 DNA with EcoRI were incubated for one hour at 37° C. with a ten fold excess of enzyme units. Digestion was terminated by phenol extraction. Plasmid cloning vector DNA was dephosphorylated by incubation with calf intestinal alkaline phosphatase which was purchased from Boehringer-Mannheim Gmbh (Mannheim, Germany). DNA ligations were incubated at 16° C. overnight with a ten fold excess of T4 DNA ligase.

Recombinant pUC18 plasmids carrying the 4.1 Kb EcoRI chromosomal DNA fragment were identified by in situ hybridization with a radiolabelled 1.4 Kb KpnI restriction fragment of the wild type hom-thrB operon as follows. Chromosomal DNA isolated from *C. glutamicum* R102 was digested with the following restriction enzymes; BamHI, BclI, EcoRI, HindIII, KpnI, PstI, SalI, SmaI, SphI, SacI. The restriction fragments. were resolved on a 0.8% agarose gel. The nucleic acids were transferred in situ to a nitrocellulose filter according to Sambrook et al., Molecular Cloning: A Laboratory Manual 1987. As. a probe, nick-translated radio-active DNA was prepared from gel purified 1.4 Kb KpnI generated restriction fragment of plasmid pRA1 (encoding the COOH terminus of the wild type hom gene and the $NH_2$ terminus of the thrB gene) also as described by Sambrook et al. Radioactively labelled [$\alpha^{32}P$]-dCTP was supplied by Amersham Corp. (Arlington Heights, Ill.). Several thousand recombinant clones were screened, but only one positive clone was identified. This plasmid was designated pJD1. The restriction map for pJD1 is shown in FIG. 2.

The $hom^{dr}$-thrB operon encoded on plasmid pJD1 was subcloned as a 3.3 Kb SalI restriction fragment encoding the $hom^{dr}$-thrB operon and its promoter into the unique SalI site of the broad host range *C. glutamicum-E. coli* plasmid pMF33 as shown in FIG. 2. The plasmid pMF33 is a broad host range pSR1 replicon exhibiting kanamycin resistance. The operon was inserted counter to the lac promotor in pMF33. This plasmid was designated pJD4 as shown in FIG. 2.

Plasmid pJD4 was introduced by transformation into *E. coli* cells and *C. glutamicum* AS019E12, a restriction-deficient prototroph of AS019 to confirm the predicted over-expression of the cloned hom$^{dr}$ gene in *C. glutamicum*. *E. coli* cells were transformed with plasmid DNA as described by Cohen et al., *Proc. Natl. Acad. Sci.* 69:2110–2115 (1973). *C. glutamicum* AS019 and AS019E12 cells were transformed with plasmid DNA according to the method of Yoshihama et. al., *J. Bacteriol.* 162:591–597 (1985). Verified pJD4/AS019E12 transformants were inoculated into 500 ml MMCG medium supplemented with 50 μg/ml kanamycin to select for the presence of the kanamycin resistant plasmid. After overnight growth at 30° C., the activity of the homoserine dehydrogenase from crude cell extracts of these cultures were determined in the presence and absence of L-threonine. The results of over-expression of the cloned deregulated enzyme in AS019E12 are shown in Table 1 above.

Homoserine dehydrogenase activity in six independent pJD4/AS019E12 isolates was demonstrated in the presence of 10 mM L-threonine, a concentration that would inactivate wild type homoserine dehydrogenase. The specific activity of the deregulated homoserine dehydrogenase (0.0596 μM ml$^{-1}$min$^{-1}$) was approximately the same as that reported for wild type (0.0450 μM ml$^{-1}$min$^{-1}$). The level of over-production of the cloned hom$^{dr}$ gene, as determined by specific activity was approximately ten fold higher than production by the chromosomally encoded hom$^{dr}$ gene. The cloned hom$^{dr}$ gene product was functional in the presence of 120 mM L-threonine.

Plasmid DNA was isolated from *E. coli* using the alkaline lysis technique of Birboim and Doly, *Nucl. Acids Res.* 7:1513–1514 (1979). Plasmid DNA was isolated from *C. glutamicum* as described by Yoshihama et al., *J. Bacteriol.* 162:591–597 (1985).

Plasmid DNA Sequencing

The complete nucleotide sequence of the hom$^{dr}$ gene and its promoter region was determined by the dideoxy-chain terminator method of Sanger et al., *Proc. Natl. Acad. Sci.* 74:5463–5467 (1977) as modified for double stranded DNA sequencing using T7 DNA polymerase (Pharmacia, Inc., Piscataway, N.J.). This method is described briefly as follows.

A double-stranded plasmid DNA sequencing template was prepared by the alkaline lysis technique of Birboim and Doly, *Nucl. Acids Res.* 7:1513–1514 (1979) as described by Sambrook et al., *Molecular Cloning: A Laboratory Manual*. Cold Spring Harbor, Cold Spring Harbor Laboratory Press 1987) from 1.7 ml of an overnight liquid culture of *E. coli* JM83 cells carrying ExoIII generated unidirectional deletion derivatives of pJD1. The presence of the plasmid was selected for by the addition of 200 μg/ml ampicillin to the medium. A 5 M sodium acetate solution of nucleic acids was extracted with phenol:chloroform. The nucleic acids were concentrated by ethanol precipitation at −20° C. The pellet was washed in 70% ethanol and dried under vacuum.

DNA annealing and sequencing reactions were as described in the Pharmacia LKB Biotechnology DNA sequence handbook (Pharmacia, Piscataway, N.J.). Radio-actively labelled [α$^{35}$S]-dATP was supplied by Amersham Corp. (Arlington Heights, Ill.).

DNA agarose gels (1.0%, 0.8%, 0.6%) were made with molecular biology grade agarose supplied by Bethesda Research Laboratories (Bethesda, Md.). Electrophoresis "E" buffer contained 40 mM tris-acetate, 1 mM EDTA, pH 8.0. DNA was visualized after staining with ethidium bromide (10 μg/ml).

DNA sequence reactions were resolved on 0.6% and 0.8% denaturing polyacrylamide gels (16"×24") at a constant 55 watts and a current of 5 Volts/cm gel length. An electrolyte salt gradient was established by the addition of sodium acetate (0.7 M) to the bottom 1×TBE buffer, the top buffer was unadulterated 1×TBE. The gels were prerun for 30 minutes prior to loading. Samples were loaded in 3% ficol, 0.05% bromophenol blue dye. Electrophoresis was continued for 3 hours and 30 minutes providing clear separation up to 300 bp from the primer start. Gels were fixed in 12% methanol, 10% glacial acetic acid, 78% water for 20 minutes. The gel matrix was dried under vacuum onto Whatmann 3MM filter paper (Kent, UK) for autoradiography at room temperature overnight.

DNA sequence data was managed using the DNA Inspector IIe program from Textco (West Lebanon, N.H.) running on a Macintosh SE/30 computer (Cupertino, Calif.).

The DNA sequence of the entire hom$^{dr}$ gene is shown in sequence 3 (SEQ ID NO:3). The carboxy terminus containing a single base pair deletion of guanosine (G) at coordinate 1964 relative to the upstream EcoRI site is shown in FIG. 4. The single base pair deletion disrupted the horn reading frame at codon 429 and caused a frameshift mutation. The amino acids after codin 429 are different from the wild type. The protein is truncated, having seven amino-acids fewer than wild type homoserine dehydrogenase.

EXAMPLE 2

Figure 5:
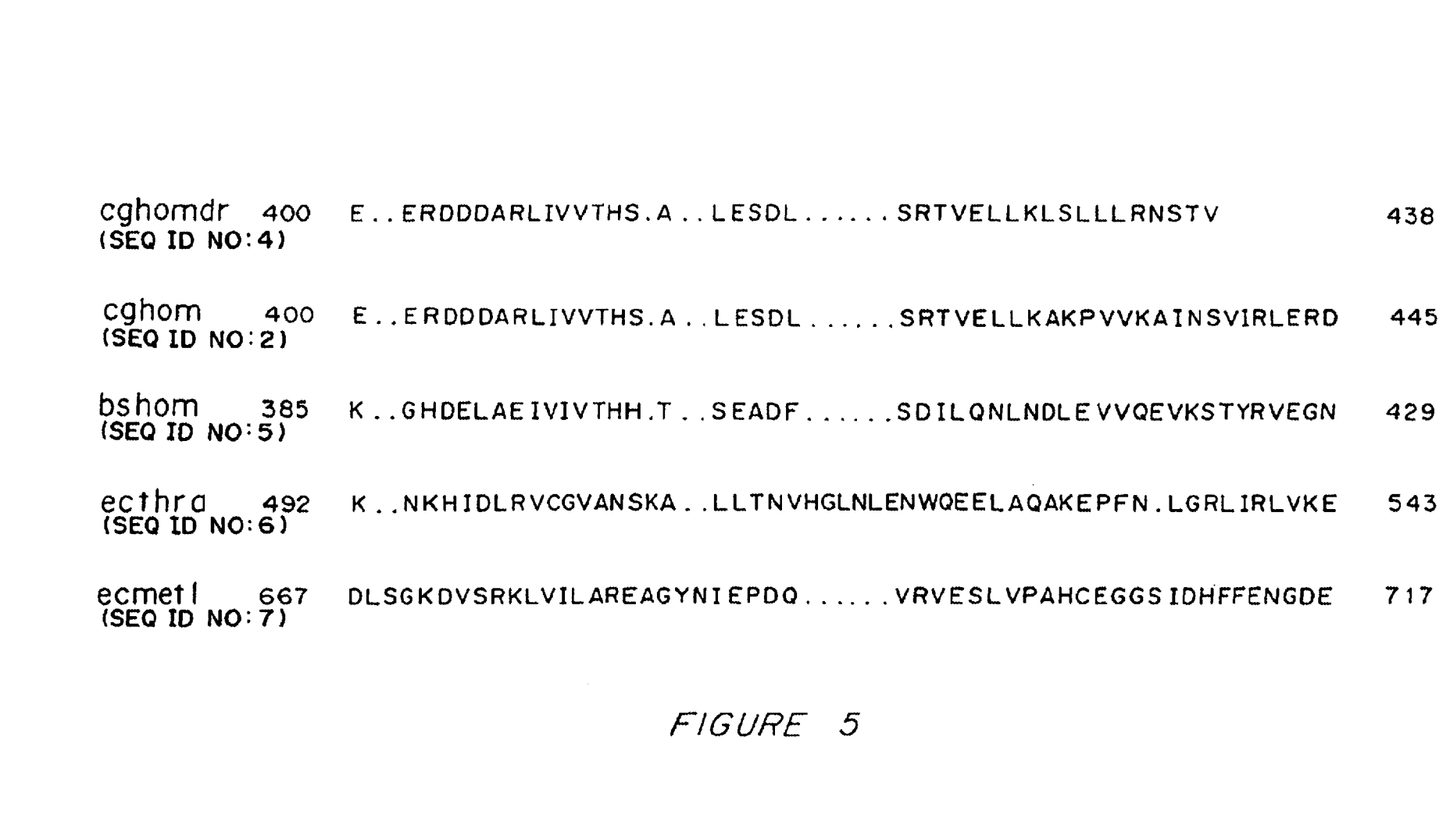
FIG. 5 is a comparison of the *C. glutamicum* deregulated (cghomdr) (SEQ ID NO:4) and wild type (SEQ ID NO:2) (cghom) homoserine dehydrogenase protein translations with those of the *B. subtilis* homoserine dehydrogenase (SEQ ID NO:5) (bshom) and the *E.coli* aspartokinase-I-homoserine dehydrogenase-I (SEQ ID NO:6) (ecthrA) and aspartokinase-II-homoserine dehydrogenase-II (SEQ ID NO:7) (ecmetl).

Homology of the Deregulated Homoserine Dehydrogenase to other Homoserine Dehydrogenases To investigate the possible relationships between the region of the homoserine dehydrogenase involved in allosteric inhibition and the other homoserine dehydrogenases, the protein sequences of the deregulated (SEQ ID NO:4) and wild type (SEQ ID NO:2) *C. glutamicum*, *E. coli* (SEQ ID NO:6 and SEQ ID NO:7), and *B. subtilis* (SEQ ID NO:5) enzymes were compared using the BESTFIT program of the University of Wisconsin Genetic Computer Group software package as shown in FIG. 5. The homoserine dehydrogenase sequences were aligned and homology optimized with spaces. The segment of the alignment covering the carboxy termini is presented in FIG. 4. A conserved amino acid sequence is centered around residues 439 to 443 in *C. glutamicum* wild type homoserine dehydrogenase. This sequence is deleted from the hom$^{dr}$ protein.

Modifications and variations of the present invention will be obvious to those skilled in the art. Such modifications and variations are intended to come within the scope of the following claims.

We claim:

1. A method for the production of threonine comprising constructing a gene isolated from a genome selected from the group consisting of *Corynebacterium glutamicum, Escherichia coli*, and *Bacillus subtilis*, encoding an enzymatically active homoserine dehydrogenase not subject to allosteric inhibition by threonine, wherein the homoserine dehydrogenase gene is mutated at the carboxy terminus, and expressing the gene to prevent end-product inhibition of threonine synthesis.

2. The method of claim 1 further comprising inserting the gene into an expression vector.

3. The method of claim 1 wherein the mutation is a single base deletion in the nucleotide sequence encoding amino acid 429 of the hom gene of *Corynebacterium glutamicum* resulting in a frameshift.

4. The method of claim 2 further comprising inserting the vector into a host for expression of the gene.

5. An enzymaticaly active homoserine dehydrogenase, isolated from bacteria selected from the group consisting of *Corynebacterium glutamicum, Escherichia coli*, and *Bacillus subtillis*, not subject to allosteric inhibition by threonine, wherein the enzyme is altered at the carboxy terminus.

6. The homoserine dehydrogenase of claim 5 wherein the enzyme is a truncated protein.

7. The homoserine dehydrogenase of claim 5 isolated from *Corynebacterium glutamicum* encoded by a gene having the following nucleotide sequence beginning at the nucleotide sequence encoding amino acid 423 of the protein:

ACC GTT GAA CTG CTG AAG CTA AGC CTG TTG TTA AGG CAA TCA ACA TGT TGA TCC GCC TCG AAA GGG ACT AAT.

8. The homoserine dehydrogenase of claim 5 isolated from *Corynebacterium glutamicum* and having the following amino acid sequence beginning at amino acid 423:

Thr Val Glu <u>Leu</u> Leu Lys Leu Ser Leu Leu Leu Arg Gln Ser Thr Val.

9. The homoserine dehydrogenase of claim 6 wherein the protein is truncated after amino acid 438.

* * * * *